(12) United States Patent
Niazi

(10) Patent No.: US 8,066,947 B2
(45) Date of Patent: Nov. 29, 2011

(54) AIR SCRUBBING SYSTEM

(76) Inventor: Sarfaraz K. Niazi, Deerfield, IL (US)

( * ) Notice: Subject to any disclaimer, the term of this patent is extended or adjusted under 35 U.S.C. 154(b) by 375 days.

(21) Appl. No.: 12/485,725

(22) Filed: Jun. 16, 2009

(65) Prior Publication Data

US 2010/0316534 A1    Dec. 16, 2010

(51) Int. Cl.
*A62B 7/08*     (2006.01)
*B01D 59/26*    (2006.01)
*B01D 53/14*    (2006.01)
(52) U.S. Cl. .............................. 422/122; 95/149; 96/290
(58) Field of Classification Search ................... 422/122; 95/149; 96/290
See application file for complete search history.

(56) References Cited

U.S. PATENT DOCUMENTS

2007/0251393 A1*  11/2007  Pope et al. ...................... 96/329
* cited by examiner

*Primary Examiner* — Kevin Joyner

(57) ABSTRACT

An air scrubber for eliminating an associated airborne contaminants and sterilizing air provided to protect against nocosomial infections, environmental allergens, weapons of biological and chemical attacks and operations requiring clean environment. The air scrubber includes a housing containing an alkali solution at pH 14 through which air passes and suspended liquid particles removed; provides are made for use in central air-conditioning systems, stand-alone applications and portable use along with respirators.

21 Claims, 4 Drawing Sheets

AIR SCRUBBING SYSTEM

BACKGROUND

Figure 1:
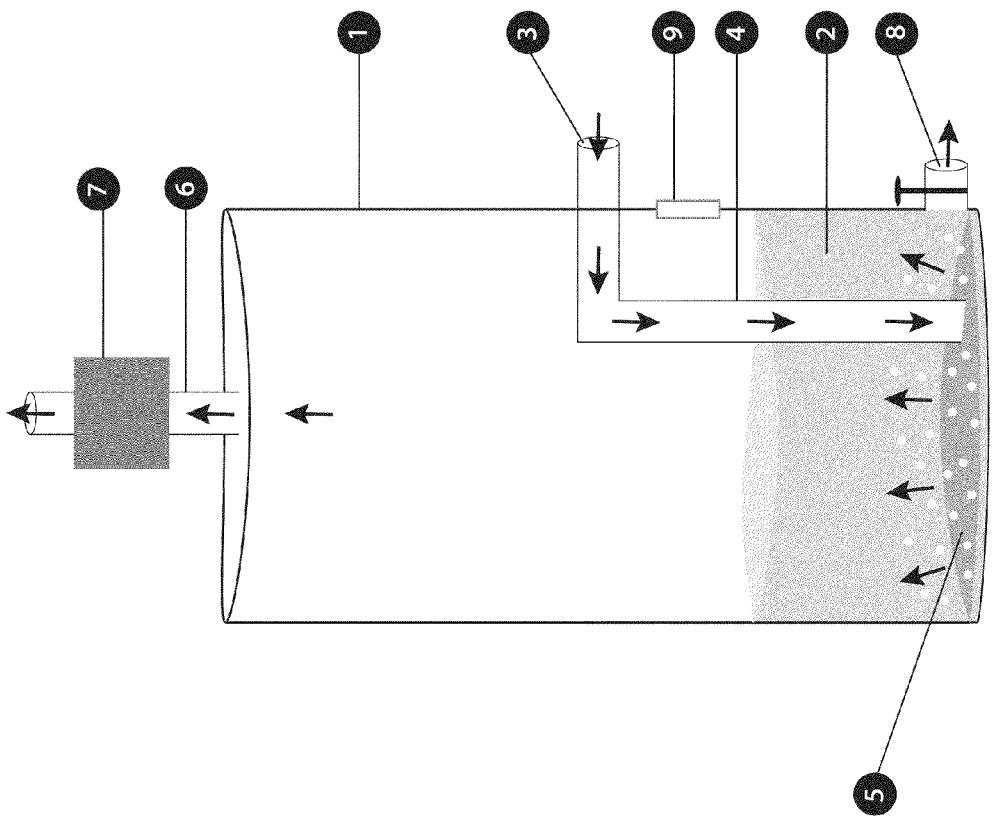

The present invention relates to an air scrubbing device for contamination removal and its uses thereof. More specifically, the present invention relates to device installed in a central air conditioning system, used as a floor or wall mountable device, or a device attached to respirators that employs an alkali solution to remove airborne contaminants (e.g., microorganisms, viruses, allergens, toxins, warfare chemicals and biological agents) from air entering the device and thus decontaminating the environment in which the device is positioned or supplying air to. Contaminants hazardous to health and interfering in a variety of manufacturing operations include:

1. Environmental Chemicals: Air contamination, particularly indoor air contamination, contributes to human health complications. Specifically, airborne chemical contaminants, particularly when present in poorly ventilated areas, cause a wide variety of human illnesses.
   a. Example chemical contaminants include, byway of non-limiting example, formaldehyde, aerosols, toluene, hydrocarbons, carbon monoxide, and the like, and are known to cause such health complications as eye irritation, headaches, nose and/or mucosal irritation, fatigue and the like.
   b. Example Biological Agents: Air contamination, particularly indoor air contamination, contributes to human health complications. Specifically, airborne biological contaminants, particularly when present in poorly ventilated areas, cause a wide variety of human illnesses. Example biological contaminants include, by way of non-limiting example, bacteria, fungi, yeast, prions, fungi spores, protozoa, viruses, algae, pollen, various antigenic agents, and the like, and are known to cause such health complications as pneumonia, fever, mycotoxicosis, various infections, asthma and the like. One of the most perplexing health problems arises from nosocomial or hospital-acquired infections from sick patients adding substantially to the cost of healthcare. Whereas general hospital working practices are aimed at reducing these infections and whereas hospitals practice isolation of dangerously infections patients, these efforts have generally been ineffective; one of the most widely known diseases resulting from nosocomial spread of infection was Legionnaires disease. The annual cost of treatment resulting from nosocomial infection in the US is between $4 Billion to $11 Billion; this cost can be substantially reduced by practicing the present invention through which the air around contaminating patients can be kept sterilized and thus preventing the spread rather than attempting to control it once it spreads through the air conditioning systems of the hospitals.
2. Environmental allergens: An important area of concern is the management of a large number of respiratory disorders emanating from allergens in the air. The pollen season wrecks havoc on the health of billions of people, adding over a $100 Billion to health care cost per year and inflicting misery to a large percentage of the world population. An allergen is typically a protein associated with a carbohydrate chain and is carried out in the air by floating particles or as pollens. While the outdoor exposure to these allergens is not preventable, the indoor environments can be made almost allergen free and to do this several devices have been suggested, mostly comprising of filtering the air either by physical filters (which remain ineffective) or by electronic precipitation, which remains extremely expensive if adequately installed.
   a. Outdoor allergens: Pollens and mold spores are outdoor allergens that float in the air and commonly trigger nasal allergy symptoms. Pollen is a microscopic, powdery substance used by plants for fertilization and reproduction. Pollens are carried between plants by wind, water, animals, bees and other insects. Nasal allergy symptoms are more often triggered by plants with small pollens that are spread by wind currents such as trees, grasses, and weeds. Generally, the pollens from brightly flowered plants with larger pollen grains don't trigger nasal allergies. Molds are microscopic members of the fungus family, which also includes mushrooms. Mold spores travel through the air like pollen. However, unlike pollen, they do not have a specific season but tend to thrive in moist situations and are affected by wind or rain. Outdoor mold spores begin to appear after a spring thaw and typically peak between July and October. In regions with mild winters, outdoor molds can be found all year long.
   b. Indoor Allergens: Indoor, or perennial, nasal allergies are triggered by another group of allergens, including dust mites, animal dander and urine, cockroach droppings, and indoor molds. Animals with fur or feathers can cause nasal allergy symptoms trigerred by saliva, proteins in animals' dander (dead skin), and urine that cause nasal allergy problems. Dust mites are microscopic creatures that live in dust and consume discarded flakes of human skin. Dust mite droppings are a common trigger of nasal allergy symptoms, and are found throughout homes, especially in parts of the home with high humidity or a concentration of human skin flakes, such as mattresses or pillows. Indoor molds thrive in dark, damp places such as basements and bathrooms. When these molds release airborne spores, they can trigger nasal allergy symptoms. Several species of cockroaches live in homes and other buildings, especially in urban areas, and especially where food and water can be found readily. Experts believe that cockroaches' bodies, as well as their feces and saliva, can trigger nasal allergies.
3. Biological Warfare Agents: Biological warfare is the deliberate use of disease and natural poisons to incapacitate humans. It employs pathogens as weapons. Pathogens are the microorganism, whether bacterial, viral or protozoic, those cause disease. There are four kinds of biological warfare agents: bacteria, viruses, rickettsiae and fungi. Biological weapons are distinguished by being living organisms, that reproduce within their host victims, who then become contagious with a deadly, if weakening, multiplier effect. Toxins in contrast do not reproduce in the victim and need only the briefest of incubation periods; they kill within a few hours. Diseases considered for weaponization, or known to be weaponized include anthrax, ebola, Marburg virus, plague, cholera, tularemia, brucellosis, Q fever, machupo, Coccidioides mycosis, Glanders, Melioidosis, Shigella, Rocky Mountain spotted fever, typhus, Psittacosis, yellow fever, Japanese B encephalitis, Rift Valley fever, and smallpox. Naturally occurring toxins that can be used as weapons include ricin, SEB, botulism toxin, saxitoxin, and many mycotoxins. Include inhaled 4. Chemical Warfare Agents: Chemical warfare is different from the use of conventional weapons or nuclear weapons because the destructive effects of chemical weapons are not primarily due to any explosive force. The offensive use of living organisms (such as anthrax) is considered biological warfare rather than chemical warfare; however, the use of nonliving toxic products produced by living organisms (e.g. toxins such as botulinum toxin, ricin, and saxitoxin) is considered chemical warfare under the provisions of the Chemical Weapons Convention. Under this Convention, any toxic chemical, regardless of its origin, is considered a chemical weapon unless it is used for purposes that are not prohibited (an important legal definition known as the General Purpose Criterion).
   a. Nerve Agents: Highly poisonous chemicals that work by preventing the nervous system from working properly: G agents (Sarin (GB), Soman (CD), Tabun (GA)), V agents, (VX)
   b. Pulmonary agents (Mustards: Distilled mustard (HD), Mustard gas (H) (sulfur mustard), Mustard/lewisite (HL), Mustard/T, Nitrogen mustard (HN-1, HN-2, HN-3), Sesqui mustard, Sulfur mustard (H) (mustard gas); Lewisites/chloroarsine agents: Lewisite (L, L-1, L-2, L-3), Mustard/lewisite (HL); Phosgene oxime (CX)
   c. Poisons that come from plants: (Abrin, Brevetoxin, Colchicine, Digitalis, Nicotine, Ricin, Saxitoxin, Strychnine, Tetrodotoxin, Trichothecene
   d. Blood Agents: Arsine (SA), Carbon Monoxide, Cyanide (Cyanogen chloride (CK), Hydrogen cyanide (AC), Potassium cyanide (KCN), Sodium cyanide (NaCN), Sodium monofluoroacetate (compound 1080)
   e. Caustics (Acids): Chemicals that burn or corrode people's skin, eyes, and mucus membranes (lining of the nose, mouth, throat, and lungs) on contact such as Hydrofluoric acid (hydrogen fluoride)
   f. Choking/Lung/Pulmonary Agents: Chemicals that cause severe irritation or swelling of the respiratory tract (lining of the nose, throat, and lungs): Ammonia, Bromine (CA), Chlorine (CL), Hydrogen chloride, Methyl bromide, Methyl isocyanate, Osmium tetroxide, Phosgene (Diphosgene (DP), Phosgene (CG)), Phosphine, Phosphorus, elemental, white or yellow, Sulfuryl fluoride.
5. Riot Control Agents/Tear Gas: Highly irritating agents normally used by law enforcement for crowd control or by individuals for protection (for example, mace): Bromobenzylcyanide (CA), Chloroacetophenone (CN), Chlorobenzylidenemalononitrile (CS), Chloropicrin (PS), Dibenzoxazepine (CR). Effective protective gear to protect against these agents while using them is required.

Specialized protections arise when exposed to above and all other agents:
   a. A variety of scientific and medical procedures result in biological contaminants that must be contained. Safety of personnel working in laboratories handling dangerous organisms is of great concern and while specific recommendations on the design of various BSL level laboratories are strictly followed, the most effective means of preventing spread of contamination is to remove it from entering any air distribution system.
   b. Clean room environment for manufacturing drugs and other products is achieved by reducing the number of particles that can carry these agents. This is an expensive and often difficult to maintain protocol. In general, biological contamination renders the air in clean rooms inappropriate for manufacturing certain drugs and dosage forms, more particularly biological drugs where removal of viruses and prions is of very high priority and is generally achieved through control of air quality comprising of HEPA filter systems that are difficult and expensive to maintain. In some instances where viral clearance is of great importance, providing sterilized air, free from viruses and prions can prove very useful and cost-effective means of increasing the safety of the products manufactured.
   c. Clean environment is also needed for surgery rooms. More particularly, the clean room environment can be created in the field or in those situations where elaborate electrical devices are impossible to install; for example, in the surgery rooms at the battle front, in parts of the world where means of providing hygienic environment are not present and in general, any operation that benefits from clean air is difficult to provide.

Prevention of exposure to above chemical and biological agents is of prime importance and a variety of measures are currently available that either selectively or generally reduces exposure or entry into body of these agents.

There is therefore an unmet need to invent a method of scrubbing air fed into air conditioning systems, in confined spaces where contaminants are present, as a first line of defense in chemical and biological weapons use and in a particularly the space where a sensitive product is manufactured and where patients need to be isolated in the event of epidemics. An invention that would resolve the unmet need would be useful in a fixed configuration as well as in a mobile situation for use in the field, examples of which include:
1. Hospital acquired infections. Fixed use in a healthcare facility to prevent cross contamination from one patient to another.
2. Allergan removal. Fixed use in a home to prevent reaction to allergens.
3. Patient Isolation. An area of medical importance is the requirement of sterile, allergan-free air for patients whose immunity has been seriously compromised and they must therefore be restricted to spaces that receive filtered air; the cost of such filtration is very high in the initial capital cost as well as the maintenance; there is thus a need to develop a highly effective, extremely low-cost device to provide this protection to patients.
4. Clean air supply in surgical theaters, manufacturing operations, etc.
5. Field use in the event of biological warfare and bioterrorism attacks. Biological warfare and bioterrorism is of major concern to many sovereign nations and billions of dollars are spent on preventing and confronting combat situations involving biological organisms. The most commonly used approach is to use specialized inhalation equipment that is often cumbersome to use, expensive to acquire and distribute and when used improperly, ineffective. The new invention should substantially reduce the cost of these preventive systems and provide a greater utility such as in the bunkers created to house personnel during an attack where the air supply can be continuously decontaminated of all types of biological agents at a very low cost.
6. Field use in the event of chemical warfare and terrorism attacks. An area of significant concerned is the protection of personnel in the event of chemical warfare attack or in the event of terrorist attacks; whereas suitable respiratory apparatus is available to protect the emergency response teams, the uncertainty in predicting the nature of biological and chemical weapons and the risk of a respirator apparatus failing can be catastrophic.

Prior art air scrubbing devices suffer from a number of problems. First, the devices are large and consume significant amounts of space and energy to be effective, the extent of which is rarely as complete as required in various sensitive areas of climate control.

The air scrubbing device of the present invention is particularly configured to overcome one or more of the aforementioned problems in removing and/or generally reducing the presence of air borne contaminants to thereby provide a safer, healthier and less infection-prone environment. The present invention also offers an extremely cost-effective approach, whose effectiveness can be further improved by combining with existing systems of HEPA filters and other control systems in practice today.

The instant invention provides a surprisingly broad range of exposure prevention that includes following features, heretofore not available in any single device:

1. Disintegration of biological organisms, spores, allergens and other resilient forms as the high pH dissolves the cell wall and otherwise disintegrates any proteins and other structures.
2. Hydrolysis of most potent organic chemicals because of the high pH effect, regardless of the solubility of compounds.
3. Neutralization of acidic components such as sulfur dioxide in the air.
4. Dissolution of water-soluble agents including gases and retention into liquid phase.

The functionality aspect of the instant invention include:

1. Fine dispersion of air into sodium hydroxide solution for maximum exposure and scrubbing action.
2. No large bubbles those are more likely to carry air droplets containing sodium hydroxide. The ceramic sparger in the device provides a critical function of dispersing air as fine bubbles in the range of 120-500 microns and thus increasing the contact of air to the surrounding sterilizing liquid;

the fine air bubbles also take longer time to rise to the surface and thus the total contact time is also increased.

3. A system of removing all airborne alkali solution droplets to reduce risk of exposure to the alkali used.
4. A means of replacing the evaporated water from the solution continuously. At 25 C vapor pressure of 10% sodium hydroxide solution is about 22 mm mercury compared to about 25 mm for water.
5. A means of draining the liquid in the container.

Chemicals have long been used in sterilization practices where heat will damage heat-sensitive materials such as biological materials, fiber optics, electronics, and many plastics. Low temperature gas sterilizers function by exposing the articles to be sterilized to high concentrations (typically 5-10% v/v) of very reactive gases (alkylating agents such as ethylene oxide, and oxidizing agents such as hydrogen peroxide and ozone). Liquid sterilants and high disinfectants typically include oxidizing agents such as hydrogen peroxide and peracetic acid and aldehydes such as glutaraldehyde and more recently o-phthalaldehyde. While the use of gas and liquid chemical sterilants/high level disinfectants avoids the problem of heat damage, users must ensure that article to be sterilized is chemically compatible with the sterilant being used. The chemicals used as sterilants are designed to destroy a wide range of pathogens and typically the same properties that make them good sterilants makes them harmful to humans. Employers have a duty to ensure a safe work environment (Occupational Safety and Health Act of 1970, section 5 for United States) and work practices, engineering controls and monitoring should be employed appropriately.

Ethylene oxide (EO or EtO) gas is commonly used to sterilize objects sensitive to temperatures greater than 60° C. such as plastics, optics and electrics. Ethylene oxide treatment is generally carried out between 30° C. and 60° C. with relative humidity above 30% and a gas concentration between 200 and 800 mg/L for at least three hours. Ethylene oxide penetrates well, moving through paper, cloth, and some plastic films and is highly effective. Ethylene oxide sterilizers are used to process sensitive instruments, which cannot be adequately sterilized by other methods. Ethylene oxide can kill all known viruses, bacteria and fungi, including bacterial spores and is satisfactory for most medical materials, even with repeated use. However it is highly flammable, and requires a longer time to sterilize than any heat treatment. The process also requires a period of post-sterilization aeration to remove toxic residues. Ethylene oxide is the most common sterilization method, used for over 70% of total sterilizations, and for 50% of all disposable medical devices.

The two most important ethylene oxide sterilization methods are: (1) the gas chamber method and (2) the micro-dose method. To benefit from economies of scale, Ethylene oxide has traditionally been delivered by flooding a large chamber with a combination of Ethylene oxide and other gases used as diluents (usually CFCs or carbon dioxide). This method has drawbacks inherent to the use of large amounts of sterilant being released into a large space, including air contamination produced by CFCs and/or large amounts of ethylene oxide residuals, flammability and storage issues calling for special handling and storage, operator exposure risk and training costs Because of these problems a micro-dose sterilization method was developed in the late 1950s, using a specially designed bag to eliminate the need to flood a larger chamber with Ethylene oxide. This method is also known as gas diffusion sterilization, or bag sterilization. This method minimizes the use of gas. Ozone is used in industrial settings to sterilize water and air, as well as a disinfectant for surfaces. It has the benefit of being able to oxidize most organic matter. On the other hand, it is a toxic and unstable gas that must be produced on-site, so it is not practical to use in many settings. Ozone offers many advantages as a sterilant gas; ozone is a very efficient sterilant because of its strong oxidizing properties (E=2.076 vs. SHE, CRC Handbook of Chemistry and Physics, 76th Ed, 1995-1996) capable of destroying a wide range of pathogens, including prions without the need for handling hazardous chemicals since the ozone is generated within the sterilizer from medical grade oxygen. The downside of using ozone is that the gas is very reactive and very hazardous. The NIOSH immediately dangerous to life and health limit for ozone is 5 ppm, much 160 times smaller than the 800 ppm IDLH for ethylene oxide. Documentation for Immediately Dangerous to Life or Health Concentrations (IDLH): NIOSH Chemical Listing and Documentation of Revised IDLH Values (as of Mar. 1, 95) and OSHA has set the PEL for ozone at 0.1 ppm calculated as an eight hour time weighted average (29 CFR 1910.1000, Table Z-1).

Chlorine bleach is another accepted liquid sterilizing agent. Household bleach consists of 5.25% sodium hypochlorite. It is usually diluted to 1/10 immediately before use; however to kill Mycobacterium tuberculosis it should be diluted only 1/5, and 1/2.5 (1 part bleach and 1.5 parts water) to inactivate prions. The dilution factor must take into account the volume of any liquid waste that it is being used to sterilize.

Bleach will kill many organisms immediately, but for full sterilization it should be allowed to react for 20 minutes. Bleach will kill many, but not all spores. It is highly corrosive and may corrode even stainless steel surgical instruments. Bleach decomposes over time when exposed to air, so fresh solutions should be made daily.

Glutaraldehyde and formaldehyde solutions (also used as fixatives) are accepted liquid sterilizing agents, provided that the immersion time is sufficiently long. To kill all spores in a clear liquid can take up to 12 hours with glutaraldehyde and even longer with formaldehyde. The presence of solid particles may lengthen the required period or render the treatment ineffective. Sterilization of blocks of tissue can take much longer, due to the time required for the fixative to penetrate.

Glutaraldehyde and formaldehyde are volatile, and toxic by both skin contact and inhalation. Glutaraldehyde has a short shelf life (<2 weeks), and is expensive. Formaldehyde is less expensive and has a much longer shelf life if some methanol is added to inhibit polymerization to paraformaldehyde, but is much more volatile. Formaldehyde is also used as a gaseous sterilizing agent; in this case, it is prepared on-site by depolymerization of solid paraformaldehyde. Many vaccines, such as the original Salk polio vaccine, are sterilized with formaldehyde.

Ortho-phthalaldehyde (OPA) is a chemical sterilizing agent that received Food and Drug Administration (FDA) clearance in late 1999. Typically used in a 0.55% solution, OPA shows better myco-bactericidal activity than glutaraldehyde. It also is effective against glutaraldehyde-resistant spores. OPA has superior stability, is less volatile, and does not irritate skin or eyes, and it acts more quickly than glutaraldehyde. On the other hand, it is more expensive, and will stain proteins (including skin) gray in color.

Hydrogen peroxide is another chemical sterilizing agent. It is relatively non-toxic when diluted to low concentrations, such as the familiar 3% retail solutions although hydrogen peroxide is a dangerous oxidizer at high concentrations (>10% w/w). Hydrogen peroxide is strong oxidant and these oxidizing properties allow it to destroy a wide range of pathogens and it is used to sterilize heat or temperature sensitive articles such as rigid endoscopes. In medical sterilization hydrogen peroxide is used at higher concentrations, ranging from around 35% up to 90%.

The best advantage of hydrogen peroxide as a sterilant is the short cycle time. Whereas the cycle time for ethylene oxide (discussed above) may be 10 to 15 hours, the use of very high concentrations of hydrogen peroxide allows much shorter cycle times. Since hydrogen peroxide is a strong oxidant, there are material compatibility issues and users should consult the manufacturer of the article to be sterilized to ensure that it is compatible with this method of sterilization. Paper products cannot be sterilized in the Sterrad system because of a process called cellulostics, in which the hydrogen peroxide would be completely absorbed by the paper product. The penetrating ability of hydrogen peroxide to not as good as ethylene oxide and so there are limitations on the length and diameter of lumens that can be effectively sterilized and guidance is available from the sterilizer manufacturers.

While hydrogen peroxide offers significant advantages in terms of throughput, as with all sterilant gases, sterility is achieved through the use of high concentrations of reactive gases. Hydrogen peroxide is primary irritant and the contact of the liquid solution with skin will cause bleaching or ulceration depending on the concentration and contact time. The vapor is also hazardous with the target organs being the eyes and respiratory system. Even short term exposures can be hazardous and NIOSH has set the Immediately Dangerous to Life and Health Level (IDLH) at 75 ppm, less than one tenth the IDLH for ethylene oxide (800 ppm). Prolonged exposure to even low ppm concentrations can cause permanent lung damage and consequently OSHA has set the permissible exposure limit to 1.0 ppm, calculated as an 8 hour time weighted average (29 CFR 1910.1000 Table Z-1). Employers thus have a legal duty to ensure that their personnel are not exposed to concentrations exceeding this PEL. Even though the sterilizer manufacturers go to great lengths to make their products safe through careful design and incorporation of many safety features, workplace exposures of hydrogen peroxide from gas sterilizers are documented in the FDA MAUDE database. When using any type of gas sterilizer, prudent work practices will include good ventilation (10 air exchanges per hour), a continuous gas monitor for hydrogen peroxide as well as good work practices and training. Further information about the health effects of hydrogen peroxide and good work practices is available from OSHA and the ATSDR.

Dry sterilization process (DSP) uses hydrogen peroxide at a concentration of 30-35% under low-pressure conditions. This process achieves bacterial reduction of 10-6 . . . 10-8. The complete process cycle time is just 6 seconds, and the surface temperature is increased only 10-15° C. (18 to 27° F.). Originally designed for the sterilization of plastic bottles in the beverage industry, because of the high germ reduction and the slight temperature increase the dry sterilization process is also useful for medical and pharmaceutical applications.

Peracetic acid (0.2%) is used to sterilize instruments.

Prions are highly resistant to chemical sterilization. Treatment with aldehydes (e.g., formaldehyde) has even shown to increase prion resistance. Hydrogen peroxide (3%) for one hour was shown to be ineffective, providing less than 3 logs reduction in contamination. Iodine, formaldehyde, glutaraldehyde and peracetic acid also fail this test (one hour treatment). Only chlorine, a phenolic compound, guanidinium thiocyanate, and sodium hydroxide reduce prion levels by more than 4 logs.

Chlorine and sodium hydroxide are the most consistent agents for prions. Chlorine is too corrosive to use on certain objects.

Silver ions and silver compounds show a toxic effect on some bacteria, viruses, algae and fungi, typical for heavy metals like lead or mercury, but without the high toxicity to humans that is normally associated with these other metals. Its germicidal effects kill many microbial organisms in vitro, but testing and standardization of silver products is yet difficult.

Alkalis (bases) like sodium hydroxide, potassium hydroxide, sodium metabisilicate and sodium bicarbonate are defined as alkalis or bases capable of forming hydroxide ions when dissolved in water giving a pH of greater than 7. Alkaline conditions inhibit the growth of microorganisms by restricting various metabolic processes; the structure and function of some macromolecules including enzymes, are particularly affected. At high concentration, alkalis cause the solubilization of bacterial cell walls and membranes and viral envelopes between pH 9 to 11. The reactions of alkalis with various types of lipoids (including phospholipids) in these membranes can be compared to their reaction with fatty acids in lipids and oils to cause salt formation (soap). Membrane disruption leads to cell wall destabilization (in case of gram negative bacteria) and loss of membrane structure and function, including disruption of the proton motive force and leakage of cytoplasm materials. Alkalis also cause breakage of peptide bonds and the breakdown of proteins, which is presumed to be the major mechanism of action against prions.

High concentration (0.5 to 2.0 N) of sodium and potassium hydroxide are used for cleaning and disinfecting manufacturing surfaces to inactivate bacteria, viruses and prion contamination. Prolonged exposure is often required to achieve ideal effect of sterilization on the surfaces treated with these alkali solutions. Alkali solutions are also effective in emulsifying and saponification of fats and removal of proteins as these are broken down to peptides and amino acids. Sodium bicarbonate is also used as a deodorizer. Higher alkalinity inhibits microorganisms, with the exception of certain thermophiles; in general, pH values greater than 9 are restrictive for growth of most vegetative organisms, including bacteria and fungi. Lower concentrations are generally inhibitory, while higher concentrations are bactericidal and fungicidal. Typical virucidal concentrations are 1-2% of sodium hydroxide and at least 4% sodium carbonate; concentrations of 1-2N of sodium hydroxide are recommended for the inactivation of prions. The main advantage of alkali use is their wide availability, low cost and a wide range of bacteriostatic and bactericidal activities obtained. More particularly, the combination of effect on fats and proteins, they offer an ideal solution to removing allergens. The disadvantages in their use include their highly corrosive nature to many surfaces, danger to human contact and the possibility of violent reaction if mixed with certain organic or inorganic substances.

The present invention provides a device for scrubbing of air through a high pH chemical solution of an alkali that can be used in confined spaces, in central air conditioning systems of patient care, home care to reduce allergies, by defense personnel as part of biological agent protection strategy, in drug manufacturing facilities and in public places to reduce spread of disease such as flu epidemic, such as the swine flu.

SUMMARY OF THE INVENTION

According to first embodiment of the present invention, an air scrubber for eliminating an associated airborne contaminant from an associated volume of air is provided. The air scrubber includes a housing including an air inlet and an air outlet, an airflow pathway initiating approximately at the air inlet of the housing and terminating approximately at the air outlet of the housing, a conduit to force air to enter at below the level of a liquid alkali used for producing sterilant effect. The sterilant source is disposed in the airflow pathway of the housing for exposing the associated airborne contaminant to the sterilant chemicals comprising a highly concentrated solution of an alkali producing pH of 10 or higher.

According to second embodiment of the present invention, a compact floor or wall mountable air-scrubbing device for eliminating an associated airborne contaminant from an associated volume of air is provided. In such instance the air-scrubbing device is fitted with means of forcing air into the device by such attachments as a variable speed fan.

According to third embodiment the present invention, a portable and compact air scrubbing device for eliminating an associated airborne contaminant from an associated volume of air is provided for use in conjunction with respiratory apparatus used in protecting against contamination with biological and chemical warfare agents, in laboratories handling highly infectious organisms and in the examination of patients with unknown highly infectious diseases such as Ebola virus or Swine flu patients. Because of its portable use where the device may be tilted accidentally, the device contains a safety system to prevent accidental flow of alkali if the device is tilted or brought into horizontal position or turned upside down. The double-walled housing volume is sufficient to retain the entire amount of alkali liquid, such instance, allowing air to pass through the system without carrying liquid alkali. The invention may be additionally equipped with electronic sensors that sense horizontal movement and shut down the air blower to prevent operations when the air is not passing through alkali.

BRIEF DESCRIPTION OF THE DRAWINGS

The aforementioned and other features and a more thorough understanding of the present invention may be achieved by referring to the following description, taken in conjunction with the accompanying drawings, wherein:

FIG. 1 is a front elevation view of a first embodiment of an air-scrubbing device, according to the present invention.

FIG. 2 is a front elevation view of a second embodiment of an air-scrubbing device, according to the present invention.

FIG. 3. is a front elevation view of a third embodiment of an air-scrubbing device, according to the present invention.

FIG. 4 is a front elevation view of a fourth embodiment of an air-scrubbing device, according to the present invention.

DETAILED DISCUSSION OF INVENTION

Disclosed according to the present invention is an air-scrubbing device and uses thereof. As will be more fully explained hereinafter, the air-scrubbing device of the present invention includes a source of liquid alkali creating high pH that, when exposed to a stream of air, exhibits a sterilant effect for removing airborne contaminants therefrom.

The high pH (around 14) in the scrubbing liquid is achieved by using a commonly available substance, sodium hydroxide as a minimum 10% solution, which has a density of 1.11, pH of 14.00 (maximum possible), boiling point of 105 C, melting point of −10 C, vapor pressure of 2.4 kPa (at 20 C, same as that of water at the same temperature).

Sodium hydroxide or similar alkali agent solutions have not been used for the purpose described in this invention and in fact, there used has been contra-indicated. Inhalation of sodium hydroxide particles or mist may cause irritation of the mouth, nose, throat, and upper respiratory tract. Tolerance to these effects may occur if exposure is recurrent or prolonged. High concentrations are very irritating to the upper respiratory tract and may result in pulmonary edema. Potential conditions resulting from long-term exposure include persistent hoarseness and reactive airway dysfunction syndrome (RADS), a chemical or irritant-induced type of asthma (Agency for Toxic Substances and Disease Registry, 2000; http://www.atsdr.cdc.gov/). Standards of inhalation exposure include:

1. Ceiling Limit (C) (not to be exceeded at any time): 2 $mg/m^3$
2. Short-Term Exposure Limit (STEL or ST): Not established.
3. 8-Hour Time Weighted Average (TWA): 2 $mg/M^3$
4. 10-Hour Time Weighted Average (TWA): Not established.
5. Immediately Dangerous to Life & Health (IDLH): 10 $mg/M^3$ However, it is important to realize that since the vapor pressure for pure sodium hydroxide is 1 mmHg at 739° C. (1362° F.), there is negligible volatility of sodium hydroxide at room temperature and all of its hazards are associated with the dissemination of powdered sodium hydroxide or solution droplets of sodium hydroxide in the air that is responsible for its hazardous effect. If means can be devised to assure that there will be no contamination of air passing through a solution of sodium hydroxide then it will be possible to construct a device that fully exploits the highly corrosive nature of sodium hydroxide to kill microorganism, inactivate spores and remove or breakdown hazardous chemicals in the air passing through it.

As will also be more fully explained, the scrubbing device is adapted to be installed in a central air conditioning system, mounted directly to a wall outlet, or attached to respiratory apparatus.

The FIG. 1 represent a first embodiment of an air-scrubbing device is shown according to the present invention. The device generally includes a housing 1 provided as a generally cylindrically elongate body adapted to be vertically disposed, a liquid alkali 2 maintained generally within the housing 1. The housing 1 houses the liquid alkali 2 and operates as a conduit through which a stream of air can be freely passed for treatment by the liquid alkali 2. More specifically, and as will be more fully explained, the housing 1 generally includes an air inlet port 3 through which a contaminated stream of air is drawn into an inner tube 4 of the housing 1 reaching almost to the bottom of housing 1, and passes through a ceramic sparger 5, which drives the contaminated stream or airflow into the liquid alkali 2 as fine bubbles. The housing 1 generally also includes an air outlet port 6 or exhaust vent through which the chemically-scrubbed or otherwise decontaminated airflow returns to the external environment subsequent to such chemical exposure after passing through a liquid-particle retaining filter 7. The housing 1 also contains a drain valve 8 to remove the liquid from the housing 1 and a port 9 to introduce alkali in solid or liquid form into housing 1. The flow path between the air inlet and air outlet generally defines an airflow pathway, as indicated by the flow arrows in FIG. 1.

Figure 2:
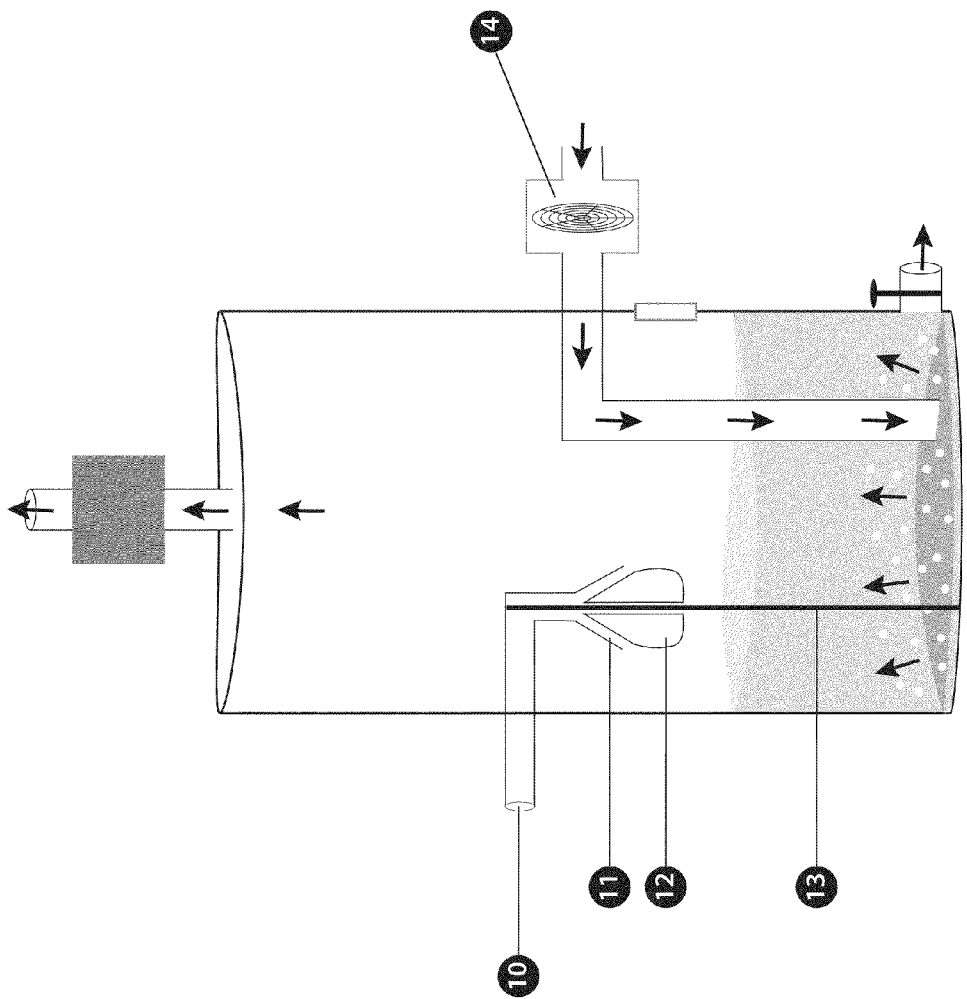

FIG. 2 represents a second embodiment where the air inlet port 3 attached to a blower fan 14 that operates to forcefully draw air into the air inlet 3 from the external environment when actuated by an on/off or variable speed switch that can be disposed on the housing 1 in a position that generally positions it for ready user access. Also shown in this embodiment is a feature to keep the level of liquid constant by providing a float ball 12 moving up or down a shaft 13 connected to a valve 11, which in turn is connected to a supply of water through a conduit 10. FIG. 2 shows air drawn into the inner housing 1, it is driven through the liquid chemical 2, and subsequently through the sparger 5 and then through the air outlet port 6 and then through filter 7.

Figure 3:
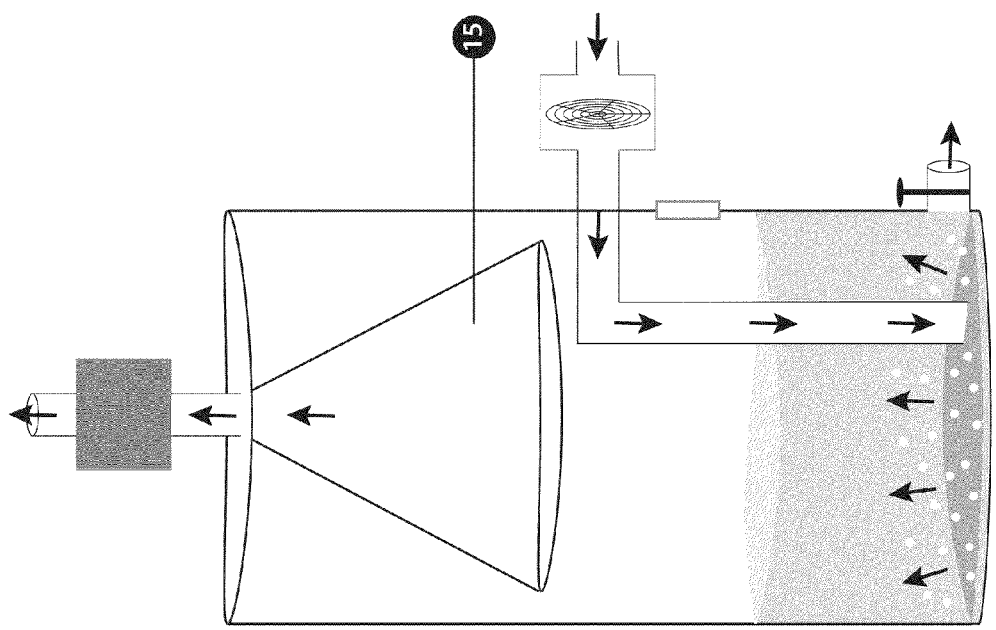

FIG. 3 shows another embodiment intended for portable use in conjunction with a respiratory apparatus wherein a housing 1 is supplied with another wall as an additional element 15, which serves a means of retaining the alkali 2 within the housing 1 if it is tilted or brought into horizontal position, it would retain alkali 2 within the housing and prevent contact with outlet port 6.

Figure 4:
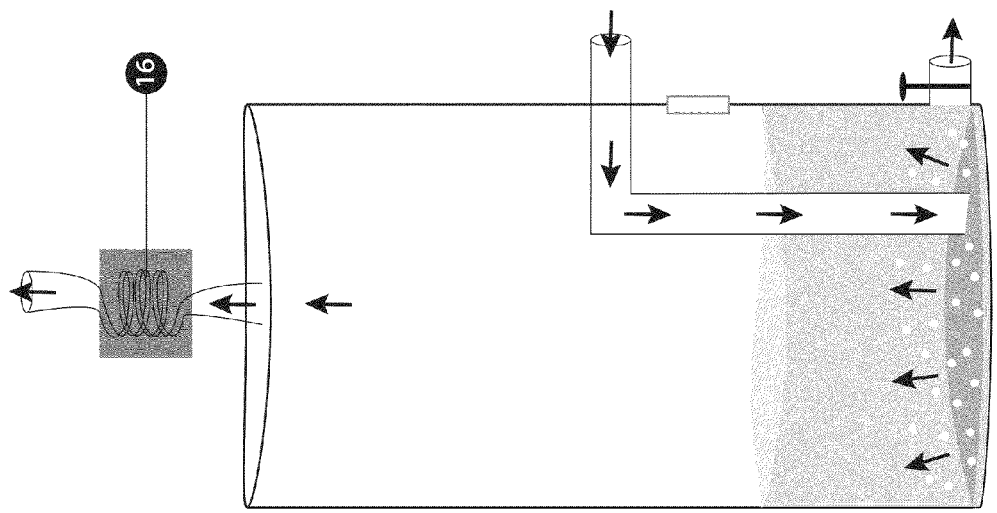

FIG. 4. Is shows another embodiment of a centrifugal force system to deposit suspended liquid particles 16 passing through which at high speed, liquid particles are deposited on the wall.

The scrubbing device may include various additional features that increase the air purification capabilities of the device. For example, the device may include at its outlet, a HEPA filter (high efficiency particulate air filter), or other physical means (e.g., activated carbon, and the like) for removing particulates from airflow. One such embodiment can be a centrifugal type separator of liquid particles in the air coming out of the outlet port, wherein the air is forced to pass through a coil wherein the diameter of the tube in the coil decreases as the distance of flow increases producing a higher pressure and forcing the liquid particles to impact on the surface of the tube in the coil.

It is to be appreciated that the air-scrubbing device of the present invention is not to be construed as limited to the foregoing discussion. It is to be appreciated that the present invention is generally directed to the concept of an air scrubber, as substantially described hereinabove. Various housing and component orientation can be provided based on aesthetics without affecting the overall effectiveness of the device. Thus, the embodiments described herein are not limited to those shown in the Figures.

It is to be further appreciated that additional modifications may be made to the invention without departing from the scope hereof. For example, the device may suitably be modified for relatively permanent association with a wall outlet More specifically, in a hospital, hotel or similar environment, it may be desirable to secure the device to a wall outlet through a mechanical fastener (e.g., screw, etc.) or other means that significantly reduces the likelihood that the device will be inadvertently or otherwise removed therefrom. The device may alternately be made part of a breathing apparatus. The device may be additionally fitted with a system that will allow retention of liquid in the even the device is tilted.

Although the invention has been described with regard to certain preferred example embodiments, it is to be understood that the present disclosure has been made by way of example only, and that improvements, changes and modifications in the details of construction and the combination and arrangement of parts may be resorted to without departing form the spirit and scope of the invention. Such improvements, changes and modifications within the skill of the art are intended to be covered by the scope of the present disclosure.

The invention claimed is:

1. An air-scrubbing device for eliminating an associated airborne biological and chemical contaminant from an associated volume of air, the air-scrubbing device comprising:
   a housing including an air inlet and an air outlet;
   an air inlet port;
   a conduit attached to the air inlet port and extending to the bottom of the housing;
   a sparging filter attached to the conduit;
   an air outlet port of the housing;
   a liquid drain port of the housing;
   an alkali inlet port;
   an airflow pathway initiating approximately at the air inlet port of the housing and terminating approximately at the air outlet port of the housing;
   a liquid chemical of pH value ranging between 8 and 14, the liquid chemical disposed in the airflow pathway of the housing for exposing the associated airborne contaminant to the liquid chemical;
   a means of removing airborne liquid particles attached to the air outlet port comprising, a housing containing a coil tube attached to said air outlet port wherein a diameter of the coil tube decreases with respect to the distance away from the air outlet port, creating a venturi separating effect to remove any suspended liquid droplets;
   a means of maintaining the level of liquid in the housing constant by continuously supplying water to make up the losses such means comprising a float ball, a valve and a conduit attached to a supply of water.

2. The air-scrubbing device claim 1 wherein said housing is constructed out of an alkali resistant material selected from a group consisting of epoxy-lined steel, 316L. stainless steel, 304L stainless steel, polyethylene, polypropylene, CPVC, butyl rubber, natural rubber, neoprene, nitrile rubber, polyvinyl chloride, fiberglass, Teflon, Viton, Saranex, 4H, Barricade, CPF 3, Responder, Trellchem HPS, and Tychem 10000.

3. The air-scrubbing device of claim 1 wherein said sparger is made of ceramic material.

4. The air-scrubbing device of claim 1 wherein said sparger is of a disc-shape.

5. The air-scrubbing device of claim 1 wherein said sparger is of a rod shape.

6. The air-scrubbing device of claim 1 wherein said sparger has pore size ranging between 10 microns to 100 microns.

7. The air-scrubbing device of claim 1 wherein said liquid alkali comprises a chemical chosen from a group of alkaline substances consisting of sodium hydroxide, potassium hydroxide, sodium bicarbonate, and sodium metabisilicate, or any combination thereof.

8. The air-scrubbing device of claim 1 wherein said liquid alkali is a sodium hydroxide solution ranging between 0.5 to 2.0 N.

9. The air-scrubbing device of claim 1, wherein said scrubbing device is attached to a re-circulating air air-handling system of a building structure such that an air intake system of the air handling system receives air coming out of the said scrubbing device and air returning from the air handling system enters through the inlet port of the scrubbing.

10. The air-scrubbing device of claim 1 further includes means of forcing air into said housing by means of a fan operated by electrical current or mechanical means and attached to the air inlet port.

11. The air-scrubbing device of claim 10 wherein said scrubbing device is used in an enclosed space to cleanse the air of the enclosed space.

12. The air-scrubbing device of claim 10 where said scrubbing device is attached to an inlet port of a breathing apparatus.

13. The air-scrubbing device of claim 10 wherein said scrubbing device is used to generate flow of sterile air over manufacturing operations.

14. The air-scrubbing device of claim 1 wherein said scrubbing device is used in biological safety laboratories to prevent escape of dangerous biological agents into atmosphere.

15. The air-scrubbing device of claim 1 wherein said scrubbing device is used in laboratories to prevent exposure of personnel to dangerous biological or chemical contaminants.

16. The air-scrubbing device of claim 1 wherein said scrubbing device is used in hospitals to prevent nocosomial infections.

17. The air-scrubbing device of claim 1 wherein said scrubbing device is attached to a central air-conditioning system of a home to prevent exposure to allergens.

18. The air-scrubbing device of claim 1 wherein said scrubbing device is attached to a breathing apparatus used in the field to prevent exposure to biological warfare agents.

19. The air-scrubbing device of claim 1 wherein said scrubbing device is attached to a breathing apparatus used in the field to prevent exposure to chemical warfare agents.

20. The air-scrubbing device of claim 1 wherein said scrubbing device is attached to an isolation chamber to re-circulate air within the chamber and thus protect patients from environmental contaminants.

21. The air-scrubbing device of claim 1 wherein said scrubbing device is attached to downdraft airflow systems used in surgery rooms to prevent infections to patients undergoing surgery.

* * * * *